United States Patent
Cohen et al.

(10) Patent No.: US 10,071,031 B2
(45) Date of Patent: *Sep. 11, 2018

(54) METHODS FOR REDUCING ORAL MALODOR IN NON-HUMAN ANIMALS

(71) Applicant: The Research Foundation for the State University of New York, Albany, NY (US)

(72) Inventors: Marvin Cohen, Saint Louis, MO (US); Susanne Cohen, Saint Louis, MO (US); Robert G. Flynn, Dupo, IL (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/227,080

(22) Filed: Aug. 3, 2016

(65) Prior Publication Data

US 2016/0338922 A1     Nov. 24, 2016

Related U.S. Application Data

(63) Continuation of application No. 14/859,691, filed on Sep. 21, 2015, now Pat. No. 9,480,635, which is a continuation of application No. 13/814,070, filed as application No. PCT/US2011/046831 on Aug. 5, 2011, now Pat. No. 9,138,428.

(60) Provisional application No. 61/371,696, filed on Aug. 7, 2010, provisional application No. 61/371,695, filed on Aug. 7, 2010.

(51) Int. Cl.
| | |
|---|---|
| A61K 8/27 | (2006.01) |
| A61K 31/435 | (2006.01) |
| A61K 8/20 | (2006.01) |
| A61K 8/22 | (2006.01) |
| A61K 8/368 | (2006.01) |
| A61K 8/49 | (2006.01) |
| A61K 8/92 | (2006.01) |
| A61Q 11/00 | (2006.01) |
| A61K 45/06 | (2006.01) |
| A61K 9/00 | (2006.01) |
| A61K 9/08 | (2006.01) |
| A61K 31/4425 | (2006.01) |
| A61K 33/20 | (2006.01) |
| A61K 33/30 | (2006.01) |
| A61K 33/40 | (2006.01) |
| A61K 8/19 | (2006.01) |
| A61K 8/34 | (2006.01) |
| A61K 8/36 | (2006.01) |
| A61K 47/02 | (2006.01) |
| A61K 47/10 | (2017.01) |

(52) U.S. Cl.
CPC .................. *A61K 8/27* (2013.01); *A61K 8/19* (2013.01); *A61K 8/20* (2013.01); *A61K 8/22* (2013.01); *A61K 8/345* (2013.01); *A61K 8/36* (2013.01); *A61K 8/368* (2013.01); *A61K 8/4926* (2013.01); *A61K 8/922* (2013.01); *A61K 9/0063* (2013.01); *A61K 9/08* (2013.01); *A61K 31/435* (2013.01); *A61K 31/4425* (2013.01); *A61K 33/20* (2013.01); *A61K 33/30* (2013.01); *A61K 33/40* (2013.01); *A61K 45/06* (2013.01); *A61Q 11/00* (2013.01); *A61K 47/02* (2013.01); *A61K 47/10* (2013.01); *A61K 2800/882* (2013.01); *A61K 2800/92* (2013.01)

(58) Field of Classification Search
USPC .................................................. 424/401; 1/1
See application file for complete search history.

(56) References Cited

U.S. PATENT DOCUMENTS

| | | | |
|---|---|---|---|
| 4,226,851 A | 10/1980 | Sompayrac | |
| 4,692,262 A | 9/1987 | Brown et al. | |
| 5,174,990 A | 12/1992 | Douglas | |
| 5,310,546 A | 5/1994 | Douglas | |
| 5,576,299 A | 11/1996 | Ando et al. | |
| 5,958,984 A | 9/1999 | Devillez | |
| 6,344,184 B1 | 2/2002 | Rolla | |
| 6,409,992 B1 * | 6/2002 | Kleinberg | A61K 8/20 424/49 |
| 6,423,300 B1 | 7/2002 | Kleinberg et al. | |
| 6,723,305 B2 | 4/2004 | DePierro et al. | |
| 6,929,790 B2 | 8/2005 | Kleinberg et al. | |
| 9,044,466 B2 | 6/2015 | Cohen et al. | |
| 2002/0150630 A1 | 10/2002 | Brooks et al. | |

(Continued)

FOREIGN PATENT DOCUMENTS

| | | |
|---|---|---|
| CN | 101780016 A | 7/2010 |
| JP | 2001/503402 A | 3/2001 |

(Continued)

OTHER PUBLICATIONS

Examiner's Search Report and Written Opinion dated May 15, 2014 issued in Singapore Application No. 201300898-2.
International Preliminary Report on Patentability dated Feb. 21, 2013 issued in PCT Patent Application No. PCT/US2011/046831.
International Preliminary Report on Patentability dated Feb. 21, 2013 issued in PCT Patent Application No. PCT/US2011/046851.
International Search Report and Written Opinion dated Oct. 19, 2012 issued in PCT Patent Application No. PCT/US2011/046851.

(Continued)

*Primary Examiner* — Yanzhi Zhang
(74) *Attorney, Agent, or Firm* — Harness, Dickey & Pierce, P.L.C.

(57) ABSTRACT

Oral compositions and methods of use thereof are provided herein. The oral compositions comprise a first component comprising at least one $E_h$-raising compound and a pharmaceutically acceptable carrier, and a second component comprising at least one zinc compound, an anti-microbial agent and a pharmaceutically acceptable carrier.

13 Claims, 3 Drawing Sheets

(56) References Cited

U.S. PATENT DOCUMENTS

| | | | |
|---|---|---|---|
| 2003/0165439 A1 | 9/2003 | DePierro et al. | |
| 2006/0140880 A1* | 6/2006 | Subramanyam | A61K 8/347 424/49 |
| 2006/0171907 A1 | 8/2006 | Scott et al. | |
| 2007/0292531 A1 | 12/2007 | Clarot et al. | |
| 2012/0034280 A1 | 2/2012 | Cohen et al. | |
| 2013/0164358 A1 | 6/2013 | Cohen et al. | |

FOREIGN PATENT DOCUMENTS

| | | |
|---|---|---|
| JP | 2002538093 A | 11/2002 |
| JP | 2008-143910 A | 6/2008 |
| WO | WO-1998/017195 A1 | 4/1998 |
| WO | WO-2000/051559 A1 | 9/2000 |
| WO | WO-2002/002128 A2 | 1/2002 |
| WO | WO-2006/069210 A2 | 6/2006 |
| WO | WO-2007/134335 A2 | 11/2007 |
| WO | WO-2009/099454 A1 | 8/2009 |
| WO | WO-2010/068444 A2 | 6/2010 |

OTHER PUBLICATIONS

International Search Report and Written Opinion dated Oct. 23, 2012 issued in PCT Patent Application No. PCT/US2011/046831.
Office Action dated Jul. 10, 2014 issued in U.S. Appl. No. 13/814,070.
Office Action dated Mar. 11, 2013 issued in U.S. Appl. No. 13/204,595.
Office Action dated Feb. 12, 2015 issued in U.S. Appl. No. 13/814,070.
Office Action dated Mar. 16, 2012 issued in U.S. Appl. No. 13/204,595.
Office Action dated Oct. 18, 2013 issued in U.S. Appl. No. 13/204,595.
Office Action dated Dec. 22, 2014 issued in U.S. Appl. No. 13/204,595.
Office Action dated Apr. 23, 2014 issued in Chinese Patent Application No. 201180039085.9—with English Translation.
Office Action dated May 24, 2012 issued in U.S. Appl. No. 13/204,595.
Office Action dated Aug. 28, 2014 issued in U.S. Appl. No. 13/204,595.
Office Action dated Jan. 29, 2015 issued in U.S. Appl. No. 13/814,070.
Office Action dated Nov. 4, 2014 issued in U.S. Appl. No. 13/204,595.
Office Action dated Sep. 5, 2014 issued in U.S. Appl. No. 13/814,070.
Office Action dated Apr. 6, 2015 issued in U.S. Appl. No. 13/814,070.
Patent Examination Report dated Mar. 14, 2014 issued in Australian Patent Application No. 2011289661.
Rölla, G., et al., (2002), "The significance of the source of zinc and its anti-VSC effect", *Int. Dent J.*, 22(52): 233-235.
Thrane, P., et al. (2007), "A New Mouthrinse Combining Zinc and Chlorhexidine in Low Concentrations Provides Superior Efficacy Against Halitosis Compared to Existing Formulations: A Double-Blind Clinical Study", *J. Clin. Dent.* 18: 82-86.

* cited by examiner ($S_1$ Water)

($S_2$ Listerine)

METHODS FOR REDUCING ORAL MALODOR IN NON-HUMAN ANIMALS

CROSS-REFERENCE TO RELATED APPLICATIONS

This application is a continuation of U.S. patent application Ser. No. 14/859,691 filed on 21 Sep. 2015, which is a continuation of U.S. patent application Ser. No. 13/814,070 filed 11 Mar. 2013, which is a national stage application of International Patent Application No. PCT/US2011/046831 filed 5 Aug. 2011, which claims the benefit of U.S. Provisional Application No. 61/371,695 filed on 7 Aug. 2010 and U.S. Provisional Application No. 61/371,696 filed on 7 Aug. 2010. The disclosure of each of the applications identified in this paragraph is incorporated herein by reference in its entirety.

FIELD

The present disclosure relates generally to oral compositions, oral care systems and methods of using the same. More particularly, the present disclosure relates to oral compositions comprising at least one $E_h$-raising compound and at least one zinc compound, and methods of using the same. In a particular embodiment, cetylpyridinium chloride (CPC), $C_{21}H_{38}NCl$, is also included in the oral composition.

BACKGROUND

This section provides background information related to the present disclosure which is not necessarily prior art.

The hard and soft tissues of the mouth are covered with microbial populations that include bacteria having different metabolic capabilities where the microbial populations may include both Gram-positive bacteria and Gram-negative bacteria. Generally, Gram-positive aerobic bacteria readily catabolize carbohydrates to produce acids which attack the hard tissues of the oral cavity, and which over time may result in the formation of dental carious lesions (cavities). In contrast, Gram-negative anaerobic bacteria readily metabolize various amino acids included in salivary peptides and proteins to form end-products which favor a formation of oral malodor and gingivitis-periodontitis. This process of peptide, protein and amino acid degradation by the mouth bacteria is referred to as oral bacterial putrefaction. The mixture of malodorous compounds produced by the Gram-negative anaerobic bacteria during putrefactive degradation of proteins, peptides and amino acids include hydrogen sulfide, methyl mercaptan, and dimethyl sulfide (formed from the sulfur-containing amino acids cysteine, cystine and methionine); indole and skatole (formed during the metabolism of tryptophan); cadaverine and putrescine (produced from lysine and ornithine); and butyrate and valerate (produced from the metabolism of other amino acids). The production of these malodorous compounds in the oral cavity results in a condition commonly referred to as oral malodor.

Hydrogen sulfide, methyl mercaptan, butyrate and propionate are putrefaction end-products that also have cell and tissue altering non-inflammatory roles in the periodontitis process. Hydrogen sulfide and methyl mercaptan are compounds particularly effective in facilitating the toxins and other-penetrability of oral epithelium by large molecular weight compounds produced by Gram-negative anaerobic bacteria, and leading to the inflammation and tissue degradation characteristics of gingivitis and periodontitis. Gingivitis is a condition in which the gingiva is red, swollen and bleeding. If left untreated, gingivitis may develop into periodontitis, a condition characterized by destruction of the periodontium, including epithelial attachment loss, periodontal membrane and ligament destruction, and loss of gingiva and alveolar bone. Severe periodontitis resulting in deep periodontal pockets may ultimately result in tooth loss.

Previous studies have largely focused on the use of germicidal agents to treat gingivitis-periodontitis and oral malodor. These studies have not recognized that gingivitis-periodontitis and oral malodor arise from a common process, namely oral bacterial putrefaction; and also that this putrefaction can be inhibited by simultaneously lowering the ability of the oral bacteria to reduce the oxidation-reduction potential ($E_h$) of the oral cavity and at the same time, raising the existing $E_h$ to where the oral environmental $E_h$ is not conducive to oral putrefaction and oral disease production.

U.S. Pat. No. 6,929,790 to Kleinberg et al., which is a continuation application of U.S. Pat. No. 6,423,300 which is a divisional application of U.S. Pat. No. 6,409,992, reports an oral composition comprising a zinc compound and at least one $E_h$ raising compound.

U.S. Pat. No. 6,723,305 to DePierro et al. reports an oral composition comprising a zinc compound and CPC.

SUMMARY

This section provides a general summary of the disclosure, and is not a comprehensive disclosure of its full scope or all of its features.

Generally, an oral composition is provided herein. The oral composition is capable of inhibiting the formation of sulfur-containing compounds, reducing oral malodor and gingivitis, reducing the formation of dental caries, inhibiting plaque formation and reducing the formation of plaque and tartar (calculus). Further, an oral care system comprising an oral composition described herein is also provided.

In one embodiment, there is provided an oral composition comprising: a first component comprising at least one $E_h$-raising compound and a pharmaceutically acceptable carrier, and a second component comprising at least one zinc compound, cetylpyridinium chloride (CPC) and a pharmaceutically acceptable carrier.

In a particular embodiment, the first and second components are stored separately.

In some embodiments, the oral composition further comprises xylitol and/or other oral health ingredients.

In yet another embodiment there is provided a method for reducing oral malodor, treating or alleviating dental diseases, reducing plaque and reducing canker sores. The methods comprise delivering the oral composition to an oral cavity in a subject. The subject may be human or a non-human animal.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The figures described herein are for illustrative purposes only of selected embodiments and not all possible implementations, and are not intended to limit the scope of the present disclosure.

DETAILED DESCRIPTION

Figure 1:
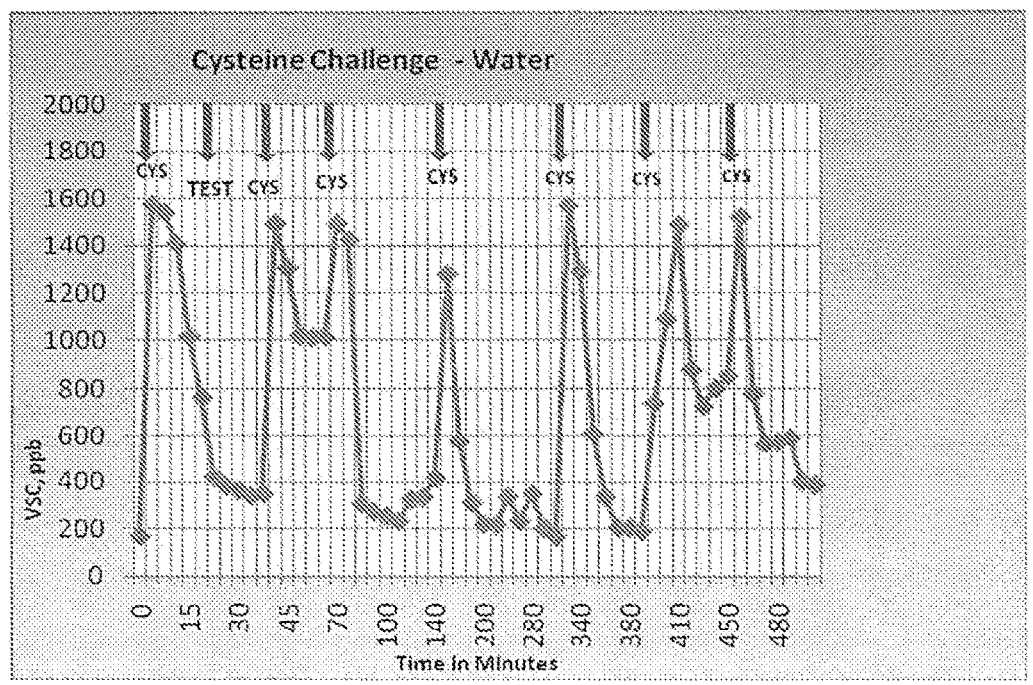
FIG. 1 is a graphical representation of volatile sulfur compounds (VSCs) in units of parts-per-billion (ppb) as measured by a Halimeter, where the subjects were tested with distilled water. The vertical axis is VSCs in ppb and the horizontal axis is time in minutes.

Example embodiments will now be described more fully with reference to the accompanying drawings.

In one embodiment, there is provided an oral composition that is formed by bringing into contact, such as by mixing, a first component and a second component described herein. The term "oral composition" is intended to include various embodiments of compositions that are useful for all aspects of oral hygiene including, but not limited to, preventing and/or treating oral disease, maintaining oral health, reducing or eliminating bad breath (oral malodor), whitening teeth, preventing gum deterioration, and/or preventing tooth decay. More particularly, the oral composition facilitates preventing oral bacteria from reducing the oxidation-reduction potential ($E_h$) of an oral cavity and, at the same time, facilitates increasing the existing oxidation-reduction potential to a level, wherein an oral environment is created that is not conducive to oral putrefaction and oral disease production. Further, the oral composition can be used for inhibiting the formation of sulfur-containing anions, reducing gingivitis, reducing the formation of dental caries, reducing canker sores, inhibiting plaque formation, and/or reducing plaque and tartar (calculus) formation.

The first component comprises at least one $E_h$-raising compound. An $E_h$-raising compound, as defined herein, is a compound capable of directly or indirectly raising the $E_h$ of the oral cavity. Non-limiting examples of $E_h$-raising compounds include oxidation reduction buffers; hydrogen peroxide; an oxyhalogen compound, such as sodium chlorite and sodium bromite; and commercially feasible combinations thereof. Additional examples of $E_h$-raising compounds include fermentable sugars, such as glucose, galactose, gulose, fructose, maltose, lactose and sucrose. Fermentable sugars, when metabolized by oral bacteria and in particular, oral streptococci, in the presence of oxygen, may produce, inter alia, hydrogen peroxide.

In one embodiment, the concentration of the $E_h$-raising compound in the first component may range from about 0.01% (100 ppm) to about 3.0% (30,000 ppm), particularly about 0.04% (400 ppm) to about 1.2% (12,000 ppm), and more particularly about 0.06% (600 ppm) to about 0.6% (6,000 ppm). In particular embodiments, the concentration of the $E_h$-raising compound is about 0.01% (100 ppm) or about 0.02% (200 ppm) or about 0.03% (300 ppm) or about 0.04% (400 ppm) or about 0.05% (500 ppm) or about 0.06% (600 ppm) or about 0.07% (700 ppm) or about 0.08% (800 ppm) or about 0.09% (900 ppm) or about 0.1% (1000 ppm) or about 0.2% (2000 ppm) or about 0.3% (3000 ppm) or about 0.4% (4000 ppm) or about 0.5% (5000 ppm) or about 0.6% (6000 ppm) or about 0.7% (7000 ppm) or about 0.8% (8000 ppm) or about 0.9% (9000 ppm) or about 1.0% (10,000 ppm) by weight of the first component.

Additionally, the concentration of the $E_h$-raising compound in the oral composition may range from about 0.005% (50 ppm) to about 1.5% (15,000 ppm), particularly about 0.02% (200 ppm) to about 0.6% (6,000 ppm), and more particularly about 0.03% (300 ppm) to about 0.3% (3,000 ppm) by weight of the oral composition.

In some embodiments, a chlorine-containing compound can be added to the first component. In a particular embodiment, a chlorine-containing compound can be added to the first component when the $E_h$-raising compound is hydrogen peroxide or a fermentable sugar in an amount sufficient to inhibit catalase(s) in the oral cavity from breaking down hydrogen peroxide or fermentable sugar. The chlorine-containing compound can be capable of inhibiting the catalase activity in the oral cavity. Suitable chlorine-containing compounds in the various oral compositions include, alkali metal chloride salts and alkaline earth metal chloride salts, such as, for example, NaCl and $CaCl_2$.

In one embodiment, the concentration of the chlorine-containing compound in the first component ranges from about 0.5% (500 ppm) to about 2.5% (2500 ppm) by weight of the first component, particularly from about 0.7% (700 ppm) to about 2.3% (2300 ppm), and even more particularly from about 1.0% (1000 ppm) to about 2.0% (2000 ppm) by weight of the first component. In particular embodiments, the concentration of the chlorine-containing compound is about 1.0% (1000 ppm) or about 1.2% (1200 ppm) or about 1.4% (1400 ppm) or about 1.6% (1600 ppm) or about 1.8% (1800 ppm) or about 2.0% (2000 ppm) by weight of the first component.

Additionally, the concentration of the chlorine-containing compound in the oral composition may range from about 0.25% (250 ppm) to about 1.25% (1250 ppm) by weight of the oral composition, particularly from about 0.35% (350 ppm) to about 1.15% (1150 ppm), and even more particularly from about 0.5% (500 ppm) to about 1.0% (1000 ppm) by weight of the oral composition.

The second component comprises at least one zinc compound. The zinc compound may be any compound capable of providing freely available zinc ions. Without being bound by theory, it is believed that the freely available zinc ions are capable of inhibiting a decrease of the $E_h$ in the oral cavity. Unbound zinc ions provide freely available zinc ions, and therefore have a greater reaction with $E_h$-lowering enzymes within the oral cavity than bound zinc ions. Specifically, these freely available zinc ions may inhibit the breakdown, by oral bacteria, of cysteine or cystine from saliva, mucosal tissues, and/or foods. As such, oral bacteria are prevented from lowering the existing $E_h$ within the oral cavity.

Non-limiting examples of zinc compounds suitable for use include any soluble zinc salt capable of providing freely available zinc ions when dissolved in water. For example, zinc chloride, zinc acetate, zinc lactate, zinc salicylate, zinc sulfate, zinc nitrate, and any possible combination thereof may be used. In a particular embodiment, the zinc compound comprises zinc chloride. In a further embodiment, the second component may comprise zinc chloride and an additional zinc compound. In further alternative embodiments, the zinc compound may comprise at least one of zinc acetate; zinc lactate; zinc salicylate; zinc sulfate; zinc nitrate; and/or any possible combination thereof.

In one embodiment, the concentration of zinc ion in the second component may range from about 0.02% (200 ppm) to about 1.0% (10000 ppm), more particularly about 0.04% (400 ppm) to about 0.7% (7000 ppm) by weight of the second component. In particular embodiments, the concentration of the zinc ion is about 0.04% (400 ppm) or about 0.05% (500 ppm) or about 0.06% (600 ppm) or about 0.07% (700 ppm) or about 0.08% (800 ppm) or about 0.09% (900 ppm) or about 0.1% (1000 ppm) or about 0.2% (2000 ppm)

or about 0.3% (3000 ppm) or about 0.4% (4000 ppm) or about 0.5% (5000 ppm) or about 0.6% (6000 ppm) or about 0.7% (7000 ppm) by weight of the second component.

Additionally, the concentration of the zinc ion in the oral composition may range from about 0.01% (100 ppm) to about 0.5% (5000 ppm), particularly from about 0.02% (200 ppm) to about 0.35% (3500 ppm) by weight of the oral composition.

In a further embodiment, the second component may also include CPC which has, among other things, anti-gingivitis and/or anti-plaque effects. CPC is a cationic surfactant having strong bactericidal and resistivity to fungi effects. Particularly, CPC is a quaternary ammonium salt that conforms generally to the formula $C_{21}H_{38}NCl$. CPC can act primarily as an anti-microbial agent by penetrating the cell membrane, which causes leakage of components in the cell, disruption of bacterial metabolism, inhibition of cell growth, and finally cell death.

To be considered therapeutically effective as an anti-gingivitis/anti-plaque product, the active ingredient must demonstrate that it is statistically substantially equivalent to the standard formulation and statistically superior to the negative control as assessed by reasonable statistical analyses (see, Fed. Reg. Vol. 68, No. 103, which is hereby incorporated by reference in its entirety, see particularly pp. 32240-41 and pp. 32247-48).

In one embodiment, the concentration of CPC in the second component may range from about 0.02% (200 ppm) to about 0.6% (6000 ppm), more particularly from about 0.09% (900 ppm) to about 0.2% (2000 ppm) by weight of the second component. In particular embodiments, the concentration of CPC is about 0.09% (900 ppm) or about 0.1% (1000 ppm) or about 0.2% (2000 ppm) by weight of the second component.

Additionally, the concentration of CPC in the oral composition may range from about 0.01% (100 ppm) to about 0.3%, (3000 ppm), particularly from about 0.045% (450 ppm) to about 0.1% (1000 ppm) by weight of the oral composition. For example, in some embodiments, the concentration of CPC is about 0.05% (500 ppm) or about 0.06% (600 ppm) or about 0.07% (700 ppm) or about 0.08% (800 ppm) or about 0.09% (900 ppm) or about 0.1% (1000 ppm) by weight of the oral composition.

In one embodiment, the second component comprises about 0.02% (200 ppm) by weight to about 1.0% (10,000 ppm) by weight of zinc ion and about 0.02% (200 ppm) by weight to about 0.6% (6,000 ppm) by weight of CPC.

In a particular embodiment, the second component comprises about 0.04% (400 ppm) by weight to about 0.7% (7000 ppm) by weight of zinc ion and about 0.09% (900 ppm) by weight to about 0.2% (2000 ppm) by weight of CPC.

It is contemplated herein that any of the $E_h$-raising compounds listed above can be used in combination with any of the zinc compounds listed above. For example, any of the $E_h$-raising compounds listed above can be used in the first component, while any of the zinc compounds listed above can be used in the second component. There may be trace amounts of each in each component. For example, an oral composition is provided comprising:

a first component comprising at least one $E_h$-raising compound selected from the group consisting of an oxidation reduction buffer; hydrogen peroxide; an oxyhalogen compound, such as sodium chlorite and sodium bromite; and combinations thereof; and wherein the first component optionally contains at least one chlorine-containing compound selected from the group consisting of an alkali metal chloride salt and an alkaline earth metal chloride salt, such as NaCl and $CaCl_2$; and a second component comprising at least one zinc compound selected from the group consisting of zinc chloride; zinc acetate; zinc lactate; zinc salicylate; zinc sulfate; zinc nitrate; and combinations thereof; and optionally CPC.

In one embodiment, the oral composition comprises a first component comprising hydrogen peroxide and optionally sodium chloride and optionally CPC; and a second component comprising zinc chloride and optionally CPC.

In one embodiment, the oral composition comprises a first component comprising a fermentable sugar and optionally sodium chloride and optional CPC, and a second component comprising zinc chloride and optionally CPC.

In one embodiment, the oral composition comprises a first component comprising sodium chlorite and optionally sodium chloride and optionally CPC; and a second component comprising zinc chloride and optionally CPC.

In one embodiment, the oral composition comprises: about 0.01% by weight to about 3.0% by weight of an $E_h$-raising compound; about 0.02% by weight to about 1.0% by weight of zinc ion; about 0.02% by weight to about 0.6% by weight of CPC; and at least one pharmaceutically acceptable carrier.

In one embodiment, the oral composition comprises about 0.5% by weight to about 2.5% by weight of the chlorine-containing compound, and wherein the second component comprises about 0.02% by weight to about 1.0% by weight of zinc ion and about 0.02% by weight to about 0.6% by weight of CPC.

In a particular embodiment, the oral composition is prepared by mixing a first component comprising the $E_h$-raising compound and a pharmaceutically acceptable carrier and a second component comprising the zinc compound, CPC and a pharmaceutically acceptable carrier.

In various embodiments, the oral composition can also include additional components such as, for example, at least one of essential oils, a desensitizing agent; a whitening agent; an anti-microbial agent; an antibiotic and/or anti-fungal agent; an anti-viral agent; an anti-cavity agent; an anti-plaque agent; an anti-tartar agent; an antioxidant; an anti-inflammatory; a deodorizer; a polishing agent; a detergent; a film-forming agent; a mineralizer or remineralizer; an agent to reduce or alleviate dry mouth; a coloring agent; a humectant; a sweetener; and/or flavorings.

For example, in one embodiment an oral composition according to the invention can comprising: a first component comprising at least one $E_h$-raising compound; a second component comprising at least one zinc compound; a third component selected from the group consisting of essential oils; a whitening agent; cetylpyridinium chloride; an anti-microbial agent; an anti-fungal agent; an anti-viral agent; an antioxident agent; an anti-cavity agent; an anti-plaque agent; a desensitizing agent; and an agent to alleviate or reduce dry mouth; and a pharmaceutically acceptable carrier.

In a particular embodiment, the first component comprises sodium chlorite or hydrogen peroxide; the second component comprises a zinc compound selected from the group consisting of zinc chloride, zinc acetate, zinc salicylate, zinc sulfate, and zinc nitrate; and the third component is selected from the group consisting of essential oils; a whitening agent; or cetylpyridinium chloride.

In one embodiment, the oral composition further comprises essential oils. For example, essential oils may comprise eucalyptol, menthol, methyl salicylate, and thymol.

In one embodiment, the oral composition further comprises a desensitizing agent. Suitable desensitizing agents for use in the oral composition include, for example, benzocaine, potassium nitrate; potassium fluoride; strontium chloride; potassium chloride; potassium citrate; iron oxalate; sodium nitrate; lithium nitrate; magnesium nitrate; calcium nitrate; calcium hydroxide; dibasic calcium phosphate; strontium acetate; sodium monofluorophosphate; bisabolol; a local or systemic analgesic agent such as NSAIDS, aspirin, acetaminophen and/or codeine; and combinations thereof.

In one embodiment, the oral composition further comprises a whitening agent. Suitable whitening agents for use in the oral composition include, for example, peroxides, pH-raising agents, sodium hypochlorite and salts thereof, and combinations thereof. For example, urea peroxide or carbamide peroxide, hydrogen peroxide, sodium bicarbonate, and combinations thereof.

In one embodiment, the oral composition further comprises an anti-microbial agent. Suitable anti-microbial agents for use in the oral composition include, for example, chlorhexidine, an anti-bacterial Gram-positive aerobic agent, an anti-bacterial Gram-negative agent, bromochloroprene, 1,6-bis(p-chlorophenyldiguanido) hexane, and water-soluble salts thereof, such as digluconate, diacetate, dilactate, dichlorohydrate; 1,6-di(2-ethylhexyldiguanido)hexane and 1,6-di(2-ethylhexyldiguanido)hexetidine, and water-soluble salts thereof; 1,6-di(2-benzyldiguanido)hexane, 1,6-di(2-benzyldiguanido)hexamidine, p-chlorophenyl-diguanide, N-(4-chlorobenzyl)-N5-(2,4-dichlorobenzyl) oliguanide, and water-soluble salts thereof such as biguanide; betanapthol, chlorothymol, thymol, anethole, eucalyptol, carvacrol, menthol, phenol, amylphenol, hexylphenol, heptylphenol, octylphenol, hexylresorcinol, hexachlorophene [2,2-methylene bis(3,4,6-trichlorophenol)], 1,1'-hexamethylene bis(5–)p-chlorophenyl)biguanide), methyl salicylate, and salts thereof; quaternary ammonium salt compounds such as morpholinium tetradecylsulfate, laurylpyridinium chloride, myristylpyridinium chloride, cetylpyridinium fluoride, cetylpyridinium chloride, cetylpyridinium bromide, cetylpyridinium iodide, stearylpyridinium chloride, dodecyltrimethylammonium chloride, tetradecyltrimethylammonium chloride, hexadecyltrimethylammonium bromide, $C_{12}$-$C_{16}$ benzyldimethylammonium chloride (benzethonium chloride), phenoxyethyldodecyldimethylammonium bromide (domiphen bromide), triclobisonium chloride, benzoic acid, sodium benzoate, potassium benzoate boric acid, tyrothricin, gramicidin, triclosan, mutanase, dextranase, stannous fluoride and combinations thereof.

In one embodiment, the oral composition further comprises other anti-microbials such as antibiotic agents and/or anti-fungal agents. Suitable antibiotic and/or anti-fungal agents for use in the oral composition include, for example, amoxicillin, amoxicillin-clavulanate, clindamycin, doxycycline, metronidazole, metronidazole-spiramycin, and combinations thereof.

In one embodiment, the oral composition further comprises an anti-viral agent. Suitable anti-viral agents for use in the oral composition include, for example, abacavir, aciclovir, acyclovir, adefovir dipivoxil, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, entry inhibitors, famciclovir, a fixed dose combination (anti-retroviral), fomivirsen, fosamprenavir, foscarnet, fosfonet, a fusion inhibitor, ganciclovir, ibacitabine, imunovir, idoxuridine, imiquimod, indinavir, inosine, integrase inhibitor, interferon type III, interferon type II, interferon type I, interferon, lamivudine, lopinavir, loviride, maraviroc, morozydine, methisazone, nelfinavir, nevirapine, nexavir, nucleoside analogues (nucleoside-analog reverse transcriptase inhibitors), oseltamivir, peginterferon alfa-2a, pegylated interferon alfa, penciclovir, peramivir, pleconaril, podofilox, podophyllotoxin, protease inhibitor, pyramidine, raltegravir, a reverse transcriptase inhibitor, ribavirin, rimantadine, ritonavir, saquinavir, stavudine, a synergistic enhancer (anti-retroviral), tea tree oil, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

In one embodiment, the oral composition further comprises an anti-cavity agent. Suitable anti-cavity agents for use in the oral composition include, for example, fluoride, sodium fluoride, sodium monoflourophosphate, nicomethanol fluorhydrate, stannous fluoride, ammonium fluoride, potassium fluoride, aluminum fluoride, calcium fluoride, cuprous fluoride, barium fluoride; organic fluorides such as long-chain amine fluorides, fluorophosphates, aluminum difluorophosphate, sodium fluorozirconate, potassium fluorozirconate, tin fluorozirconate, sodium silicofluoride, fluorinated sodium calcium pyrophosphate, green tea, spirulina algae, and combinations thereof.

In one embodiment, the oral composition further comprises an anti-plaque agent. Suitable anti-plaque agents for use in the oral composition include, for example, an alcohol such as ethanol, triclosan, sanguinarine, hexetidyne, zinc citrate, a fluoride, sodium lauryl sulfate, zinc phosphate, zinc acetate, zinc aspartate, zinc acetylmethionate, zinc citrate trihydrate, zinc tannate, zinc gluconate, zinc lactobionate, zinc maltobionate, zinc hydrolyzed collagen, zinc pyrrolidone carboxylic acid, zinc tribromosalicylanfiide, zinc caprylate, zinc octoate, zinc laurate, zinc myristate, zinc stearate, zinc oleate, zinc carbonate, zinc borate, zinc silicate, zinc sulfide, zinc sulfate, zinc oxide, zinc phenol sulfonate, zinc stannate, zinc dl-lactate, trihydrate, tannic acid, citric acid, acetic acid, lactic acid, sodium trihydrogen pyrophosphate, disodium dihydrogen pyrophosphate, trisodium hydrogen pyrophosphate, trisodium hydrogen pyrophosphate monohydrate, trisodium hydrogen pyrophosphate nonahydrate, tetrasodium pyrophosphate, tetrasodium pyrophosphate decahydrate, potassium trihydrogen pyrophosphate, dipotassium dihydrogen pyrophosphate, tripotassium hydrogen pyrophosphate, tetrapotassium pyrophosphate, diammonium dihydrogen pyrophosphate, triammonium hydrogen pyrophosphate, triammonium hydrogen pyrophosphate monohydrate, calcium dihydrogen pyrophosphate, calcium pyrophosphate, tetraaluminium pyrophosphate, and combinations thereof.

In one embodiment, the oral composition further comprises an anti-tartar/anti-calculus agent. Suitable anti-tartar/anti-calculus agents for use in the oral composition include, for example, pyrophosphate, a zinc salt, and combinations thereof.

In one embodiment, the oral composition further comprises an antioxidant. Suitable antioxidants for use in the oral composition include, for example, vitamins, such as vitamin A, C, or E; polyphenols; tocopherols; ethylenediaminetetracetic acid; butylated hydroxytoluene (BHT); and propyl gallate.

In one embodiment, the oral composition further comprises an anti-inflammatory agent. Suitable anti-inflammatory agents for the gums include, but are not limited to, beta-glycerhetinic acid, enoxolone, salicylic acid, azulene, ginkgo biloba, witch hazel, corticosteroids, NSAIDs, and salts thereof.

In one embodiment, the oral composition further comprises an agent to reduce and/or alleviate dry mouth. Suitable agents to reduce and/or alleviate dry mouth include, but are not limited to lactoferrin, lysozyme, lactoperoxidase, immunoglobulins, colustrum extract, glucose oxidase, amylase, amyloglucosidase, glucoxidase, papain, peptizyme, aloe vera, a nature-identical flavoring component that can make the mouth water and combinations thereof.

In one embodiment, the oral composition further comprises a deodorizer. Suitable deodorizers for use in the oral composition include, for example, chlorhexidine, hydrogen peroxide, vitamin B, vitamin C, sodium bicarbonate, an herb, and combinations thereof.

In one embodiment, the oral composition further comprises a polishing agent. Suitable polishing agents for use in the oral composition include, for example, calcium carbonate, dicalcium phosphate dihydrate, aluminum hydroxide, dental grade silicas, sodium carbonate, sodium bicarbonate, potassium carbonate, potassium bicarbonate, anhydrous calcium phosphate, dicalcium phosphate, tribasic calcium phosphate, sodium phosphate, potassium phosphate, calcium pyrophosphate, insoluble sodium metaphosphate, disodium orthophosphate, dibasic sodium phosphate, magnesium hydroxide, magnesium carbonate, magnesium silicate, magnesium trisilicate, trimagnesium phosphate, monomagnesium phosphate, magnesium oxide, stannic oxide, zinc oxide, bentonite, flour of pumice, α-alumina trihydrate, alumina, aluminum silicate, zirconium silicate, hydroxyapatite, crosslinked urea-formaldehyde resin, crosslinked melamine-formaldehyde resin, polymethacrylate, polymethylmethacrylate, polystyrene, powdered polyethylene, silica gel, dehydrated silica gel, sodium glycerophosphate, sodium trimetaphosphate, organic phosphates, and combinations thereof.

In one embodiment, the oral composition further comprises a detergent. Suitable detergents for use in the oral composition include, for example, sodium lauryl sulphate, sodium lauryl sarcosinate, sodium methyl cocoyl taurate, polysorbates, sorbitan derivatives and combinations thereof.

In one embodiment, the oral composition further comprises a film-forming agent. Suitable film-forming agents to protect against tar from tobacco and other tannins, include, but are not limited to, polyethylene glycol (PEG), petrolatum, liquid paraffin, dimethicone, magnesium stearate and stearic acid.

In one embodiment, the oral composition further comprises a mineralizer or remineralizers. Suitable mineralizers or remineralizers of dental enamel include, but are not limited to, calcium in any form of mineral and organic apatite and hydroxyapatite salts.

In one embodiment, the oral composition further comprises a coloring agent. Suitable coloring agents include, but are not limited to, red, blue and green food coloring, such as FD and C-type dyes and lakes, for example D&C blue #1, D&C blue #4, D&C brown #1, D&C green #5 through #8, D&C orange #4 through #11, D&C yellow #2 through #11, D&C red #6 through #40, FD&C blue #1, FD&C blue #2, FD&C blue #4, FD&C red #3, FD&C red #4, FD&C red #33, FD&C red #40, FD&C yellow #5, FD&C yellow #6, FD&C yellow #10, FD&C orange #4, FD&C green #3, carmine, and fruit and vegetable extracts.

In one embodiment, the oral composition further comprises a humectant. Suitable humectants for use in oral composition include, but are not limited to, glycerin, propylene glycol, hydrogenated glucose syrup, polyethylene glycol-14 (PEG-14), polyethylene glycol-18 (PEG-18), polyethylene glycol-55 (PEG-55), polyethylene glycol-100 (PEG-100), polyethylene glycol-135 (PEG-135), polyethylene glycol-180 (PEG-180), polyethylene glycol-200 (PEG-4), polyethylene glycol-240 (PEG-240), polyethylene glycol-300 (PEG-6), polyethylene glycol-400 (PEG-8), polyethylene glycol-450 (PEG-9), polyethylene glycol-500 (PEG-10), polyethylene glycol-600 (PEG-12), polyethylene glycol-1540 (PEG-32), polyethylene glycol-2000 (PEG-40 or PEG-2M), polyethylene glycol-3000 (PEG-60), polyethylene glycol-4000 (PEG-75), polyethylene glycol-6000 (PEG-150), polyethylene glycol-9000 (PEG-9M or PEG-200), polyethylene glycol-20,000 (PEG-20M or PEG-350), polyethylene glycol-600,000 (PEG-14M), propylene glycol (PG), glycerol (glycerin), erythritol, xylitol, sorbitol, mannitol, lactitol, hydrogenated starch hydrolyzates.

In one embodiment, the oral composition further comprises a sweetener that both improves the taste of the oral composition and freshens breath. Suitable sweeteners for use in the oral composition include, for example, xylitol, sodium saccharin, menthol, eucalyptus, sorbitol, mannitol, saccharin, aspartame, acesulfame potassium (acesulfame K), stevia, peppermint oil, spearmint oil, and combinations thereof.

In one embodiment, the oral composition further comprises a flavoring. Suitable flavorings include, but are not limited to, menthol, eucalyptol, peppermint oil, spearmint oil, anise oil, benzaldehyde, bitter almond oil, camphor, cedar leaf oil, cinnamic aldehyde, cinnamon oil, citronella oil, clove oil, heliotropin, lavender oil, phenyl salicylate, pin oil, pin needle oil, rosemary oil, sassafras oil, thyme oil, thymol, wintergreen oil, lemon oil, orange oil, vanillin, carvone, anethole, irone, orris, carraway, coriander, pimento, eugenol, nutmeg and other flavoring oils generally regarded as safe (GRAS) by the Federal Drug and Food Administration (FDA).

Each of the first and second components further comprises one or more pharmaceutically acceptable carriers. Pharmaceutically acceptable carriers for use in oral compositions and systems are well known in the art. Non-limiting examples of suitable pharmaceutically acceptable carriers include glycerin, water, saline, dextrose, sucrose, glycerol, polyethylene glycol, ethanol, sorbitol, mannitol, xylitol, and combinations thereof.

In one embodiment, the oral composition further contains any combination of the above-described components. Such an embodiment is directed to any combination of the above-described desensitizing agents; whitening agents; anti-microbial agents; antibiotics and/or anti-fungal agents; anti-viral agents; anti-cavity agents; anti-plaque agents; anti-tartar agents; antioxidants; anti-inflammatories; an agent to reduce or alleviate dry mouth; a deodorizer; a polishing agent; a detergent; a film-forming agent; a mineralizer or remineralizer; a coloring agent; a humectant; a sweetener; and/or flavorings.

In one embodiment, an oral composition is provided wherein a first component comprises at least one $E_h$-raising compound; a second component comprises at least one zinc compound; and at least one additional (third) component selected from the group consisting of essential oils; a whitening agent, cetylpyridinium chloride or another antimicrobial agent, an anti-fungal agent, and anti-viral agent; an antioxident agent; an anti-cavity agent; an anti-plaque agent; a desensitizing agent and an agent to alleviate or reduce dry mouth; and a pharmaceutically acceptable carrier.

In one embodiment, an oral composition is provided wherein a first component comprises sodium chlorite or hydrogen peroxide; a second component comprises a zinc compound selected from the group consisting of zinc chloride, zinc acetate, zinc lactate, zinc salicylate, zinc sulfate, and zinc nitrate; and at least one further component (optionally part of the second component) comprising essential oils; a whitening agent; or cetylpyridinium chloride.

In one embodiment, an oral composition is provided wherein a first component comprises at least one $E_h$-raising compound and a pharmaceutically acceptable carrier, and a second component comprises at least one zinc compound, cetylpyridinium chloride (CPC) and a pharmaceutically acceptable carrier. In a particular embodiment, the first and second components are stored separately.

An effective amount of such combinations is determined by the particular components utilized in the oral composition. Moreover, the oral composition is not limited to the agents and components described above, but may include various other agents and components.

The pH of the oral composition of the present invention is dependent upon the particular $E_h$-raising compound and the particular zinc compound combination used. For example, when the $E_h$-raising compound is hydrogen peroxide, the pH of the oral composition ranges from about 3.0 to about 6.0. In one embodiment, the pH ranges from about 3.5 to about 5.0, and more suitably, from about 4.2 to about 4.8. An acidic pH ensures the availability of freely available zinc ions. This is because zinc ions, above a pH of about 6.0, combine with hydroxide ions in solution to form poorly soluble zinc hydroxide, thereby making freely available zinc ions less available.

On the other hand, when the $E_h$-raising compound is an oxyhalogen compound, such as sodium chlorite, a pH between about 2.0 to about 6.5, is unsuitable for the stability of sodium chlorite during its storage. At an acidic pH, unstable and less desirable chlorine dioxide is produced. The pH of the first composition during storage needs to be between about 7.0 and about 8.5 where sodium chlorite is most stable. The instability of zinc ions at a pH of 6.0 and above, and the instability of chlorite at a pH of about 6.0 and below, may make it advantageous at times to keep the first and the second compositions separate in two compartments or a two-phase system until ready for use.

In one embodiment, an oral composition is provided comprising a first component comprising about 0.04% by weight to about 1.2% by weight of sodium chlorite and the pH of the first component ranges from about 7.0 to about 8.5, and a second component comprising about 0.04% by weight to about 0.7% by weight of zinc ion and about 0.09% by weight to about 0.2% by weight of CPC and the pH of the second component ranges from about 3.0 to about 6.0.

In one embodiment, the first and second components are stored separately or substantially prevented from contact with each other, and may be brought into contact, such as by mixing with each other, by users prior to use. The components may be brought into contact about 10 seconds to about 30 minutes before use. In a particular embodiment, the first and the second components are brought into contact within about 10 minutes from use, and more particularly, within about 5 minutes from use.

Once a first and second component, as described herein, are brought into contact with each other are brought into contact with each other, some of the zinc compound dissociates into freely available zinc ions.

In one embodiment, an oral composition is provided comprising: about 0.005% by weight to about 1.5% by weight of an $E_h$-raising compound; about 0.01% by weight to about 0.5% by weight of zinc ion; about 0.01% by weight to about 0.3% by weight of CPC; and at least one pharmaceutically acceptable carrier, wherein the oral composition is prepared by mixing a first component comprising the $E_h$-raising compound and a pharmaceutically acceptable carrier and a second component comprising a zinc compound, CPC and a pharmaceutically acceptable carrier.

In another embodiment of the invention, an oral composition described herein may contain xylitol. The inclusion of xylitol can be used to facilitate decreasing periodontal disease and plaque adhesion within the oral cavity. Bacteria in the oral cavity release toxins that break down tissues, thereby facilitating the growth of infections. Specifically, bacteria assist in the creation of plaque along the gum line. Over time, continued exposure to plaque may lead to periodontal disease. Furthermore, dextrans in the oral cavity have been shown to accelerate the aggregation of bacteria, such as adhesions of plaque to teeth are increased. Xylitol facilitates reducing the formation of dextrans in the oral cavity. As such, plaque adhesion is reduced, which leads to a reduction in periodontal disease.

Furthermore, using xylitol has shown a reduction in new tooth decay, along with arrest and even reversal of existing dental caries. Specifically, xylitol suppresses at least some of the most harmful strains of oral bacteria, such that the use of xylitol may provide a long-lasting change in bacterial communities present in the oral cavity. Moreover, xylitol has the ability to enhance the mineralization of the enamel on teeth and may be used to effectively treat small decay spots on teeth. In addition, xylitol may stimulate saliva flow and help keep salivary minerals in a useful form. As such, xylitol may be utilized to increase saliva production for people suffering a dry mouth due to illness, aging, or drug side effects.

In one embodiment, xylitol is mixed with a small amount of titanium tetrafluoride to provide an enhanced effect that further reduces plaque adhesion in the oral cavity.

Furthermore, the xylitol-containing oral composition may also be useful to reduce bacteria that may cause ear, nose, and/or throat infections. Furthermore, the xylitol-containing oral composition may also be useful in reversing bone loss, decreasing insulin resistance, decreasing hypertension which can be associated with diabetes, and/or correcting hormonal imbalances.

Typically, the amount of xylitol in the oral composition will depend on the type of oral composition and the desired function of the xylitol. For example, when the oral composition is a mouth rinse, the composition may include an amount of xylitol of about 0.1% by weight to about 15% by weight of the total oral composition. In another embodiment, when the oral composition is a confectionery or a chewing gum, the oral composition may include an amount of xylitol of from about 0.1% by weight to about 50% by weight. Xylitol can be included in the first or second composition. In an alternative embodiment, the xylitol is stored separately from each of the first and second compositions.

The oral composition optionally contains xylitol and/or other components as described herein. In one embodiment, the oral composition formed further includes a concentration of xylitol ranging from about 0.1% to about 50% by weight of the composition. In a particular embodiment, the concentration of xylitol ranges from about 0.1% to about 50% by weight of the oral composition.

The oral compositions of the present disclosure may be provided in a variety of oral vehicles proper for administration to humans and/or non-human animals. For example, the oral compositions may take the form of a solid, liquid, spray, gel, foam, syrup, or powder. Additionally, the oral composition may be orally delivered through a dental care product, a food product, a tablet, capsule, a flash-melt formulation, a candy, a lozenge, a chewing gum, a confection, a toothpaste, mouthrinse, breath spray and/or a mint.

In one embodiment, the oral composition of the invention may comprise a first component and a second component, as described herein, which are stored separately, for example in separate containers or one container having separate compartments for each component. As used herein, the phrase "stored separately" refers to substantially preventing a first component and a second component from contacting each other until the desired point of use. For example, a first and second component can be contained in separate containers to substantially prevent premature contact. The term "substantially" prevent is intended to encompass both 100% physically preventing the components from contacting each other until the desired point of use, and where the components may come in to inconsequential chemical contact. Any known container or device for storing components separately can be used in the instant disclosure. For example, a syringe-like barrel can be used where the components are kept separate until the plunger is activated, a bottle, a tube, a capsule, or any equivalent thereof.

Alternatively, in another embodiment, the oral composition may be a solution where one of the first or the second components is encapsulated (or any equivalent to a capsule). For example, the first component can be a solution and the second component can be present in the solution in an encapsulated form.

In another embodiment, the oral composition may be a tablet, confectionery or a chewing gum where the first and second components are substantially prevented from contacting each other until brought into contact by for example, the user. Further examples include a two-phase tablet or capsule that can be used wherein the first component and the second component are substantially prevented from mixing or coming into contact with each other.

In another embodiment, the oral composition may be delivered to non-human animals in the form of a pet mouthwash or rinse, toothpaste, pet spray, pet treat, pet food, animal feed, and/or a chew toy.

In addition, oral administration vehicles for the oral composition are not limited to the vehicles disclosed above, but may also include any other acceptable oral delivery mechanisms.

In a further embodiment, an oral care system is provided which forms an oral composition as described in more detail below. The oral care system facilitates preventing oral bacteria from reducing an oxidation-reduction potential ($E_h$) of the oral cavity and, at the same time, facilitates increasing the existing oxidation-reduction potential to a level, wherein an oral environment is created that is not conducive to oral putrefaction and oral disease production.

In one embodiment, an oral care system comprising a first component and a second component, as described herein, is provided. In a particular embodiment, the first and second components are stored separately, or substantially prevented from contact with each other, in the oral care system.

In further embodiments, methods of using the oral care systems and oral compositions of the invention are provided.

The methods described herein involve delivering an oral composition, according to the present invention, to the oral cavity of a subject. In particular embodiments, prior to delivering the oral composition to the oral cavity, the first component and the second component are mixed as described above.

In one embodiment, a method is provided for inhibiting the formation of sulfur-containing compounds in the oral cavity and preventing the reduction of the oxidation-reduction potential of the oral cavity by delivering into the oral cavity the oral composition comprising an effective amount of zinc ions, an $E_h$-raising compound, and cetylpyridinium chloride. As defined herein, sulfur-containing compounds include, for example, sulfide, hydrogen sulfide, and methyl mercaptan. In a particular embodiment, an effective amount is sufficient to inhibit the formation of sulfur-containing compounds and/or prevent a lowering of the oxidation-reduction potential of the oral cavity. For example, an effective amount of zinc ion in a dentifrice or a mouth rinse may range from about 0.01% to about 0.5% by weight and, in a particular embodiment, about 0.02% to about 0.35% by weight of the oral composition.

In one embodiment, there is also provided a method for reducing oral malodor by delivering into the oral cavity the oral composition containing effective amounts of zinc ion, an $E_h$-raising compound and cetylpyridinium chloride. Further, a reduction or alleviation of oral malodor (bad breath), conversely can mean providing fresh or clean breath. Oral malodor can be quantified, in some circumstances, by utilizing an organoleptic (sniffing) test. Alternatively, oral malodor can be quantified by utilizing a Halimeter, which measures bad breath sulfur gases in parts per billion (ppb).

In one embodiment, the method is effective to reduce oral malodor for at least 2 hours to about 12 hours. For example, the oral composition and method of using an oral composition described herein can reduce oral malodor for at least 2 hours, preferably 3 hours, preferably 4 hours, preferably 5 hours, preferably 6 hours, preferably 7 hours, preferably 8 hours, preferably 9 hours, preferably 10 hours, preferably 11 hours, preferably 12 hours. In some embodiments, the method is effective to reduce oral malodor for more than 12 hours or at least 12 hours.

In one embodiment, there is also provided a method for preventing or alleviating dental diseases comprising delivering into the oral cavity effective amounts of zinc ion, an $E_h$-raising compound and cetylpyridinium chloride, wherein the dental diseases include, for example, gingivitis, periodontitis, and tooth decay. Without being bound by theory, it is believed that an effective amount of zinc ion, an $E_h$-raising compound and/or cetylpyridinium chloride is an amount sufficient to raise the oxidation-reduction potential of the oral cavity to normal levels. This can prevent or reduce tooth decay, gingivitis or periodontitis. For example, an effective amount of an oral composition is an amount sufficient to reduce or prevent the formation of malodorous compounds such as hydrogen sulfide and the growth of harmful Gram-negative anaerobic bacteria which may cause gingivitis and periodontitis.

In one embodiment, there is provided a method for decreasing plaque adhesion, and/or treating periodontal disease within the oral cavity, gingivitis, periodontitis and/or reducing tooth decay by delivering into the oral cavity an effective amount of the oral composition.

In one embodiment, there is provided a method for desensitizing the dentin by delivering to the oral cavity an effective amount of the oral composition. In a further embodiment, the oral composition to be delivered further contains at least one desensitizing agent, such as, but not limited to, the desensitizing agents listed above.

In one embodiment, there is provided a method for whitening teeth by delivering to the oral cavity an effective amount of the oral composition. In a further embodiment, the oral composition to be delivered further contains at least one whitening agent, such as, but not limited to, the whitening agents listed above.

In one embodiment, there is provided a method for providing an anti-microbial benefit to a subject by delivering to the oral cavity an effective amount of the oral composition. In a further embodiment, the oral composition to be delivered further contains at least one anti-microbial agent, such as, but not limited to, the anti-microbial agents listed above.

In one embodiment, there is provided a method for providing an antibiotic benefit to a subject by delivering to the oral cavity the oral composition. In a further embodiment, the oral composition to be delivered further contains at least one antibiotic agent, such as, but not limited to, the antibiotic and/or anti-fungal agents listed above.

In one embodiment, there is provided a method for reducing or preventing cavities in a subject by delivering to the oral cavity the oral composition. In a further embodiment, the oral composition to be delivered further contains at least one anti-cavity agent, such as, but not limited to, the anti-cavity agents listed above.

In one embodiment, there is provided a method for reducing plaque in a subject by delivering to the oral cavity the oral composition. In a further embodiment, the oral composition to be delivered further contains at least one anti-plaque agent, such as, but not limited to, the anti-plaque agents listed above.

In one embodiment, there is provided a method for reducing tartar/calculus by delivering to the oral cavity the oral composition. In a further embodiment, the oral composition to be delivered further contains at least one anti-tartar (anti-calculus) agent, such as, but not limited to, the anti-tartar/anti-calculus agents listed above.

In one embodiment, there is provided a method for deodorizing the oral cavity of a subject by delivering to the oral cavity the oral composition. In a further embodiment, the oral composition to be delivered further contains at least one deodorizing agent, such as, but not limited to, the deodorizing agents listed above.

In one embodiment, there is also provided a method for polishing teeth by delivering to the oral cavity the oral composition. In a further embodiment, the oral composition to be delivered further contains at least one polishing agent, such as, but not limited to the polishing agents listed above.

In one embodiment, there is provided a method for reducing or preventing gingivitis by delivering to the oral cavity the oral composition. The oral composition may contain any additional anti-gingivitis agents and/or any additional ingredients listed herein.

In one embodiment, there is provided a method for treating, alleviating or preventing or reducing the occurrence of canker sores by delivering to the oral cavity the oral composition.

In one embodiment, the oral composition can be administered from one to five times per day. In one embodiment, the oral composition can be administered three times per day, preferably two times per day, or even once per day.

In another embodiment of the invention, the compositions disclosed herein can be administered to non-human animals, such as pets. For example, any of the oral composition embodiments can be delivered to the oral cavity of a non-human animal. Further, any of the methods can be used with non-human animals, wherein the subject is a non-human animal. Examples include domestic animals, such as dogs and cats; and livestock/farm animals, such as horses, cows and pigs; or for health purposes with exotic wildlife such as animals in zoos or in their natural environments.

It has been discovered by the present inventors that CPC remains in the oral cavity for long periods after use, which may be useful in maintaining a healthy oral cavity for longer periods of time between treatments. The addition of CPC to the oral composition demonstrates a definite, additional effectiveness.

It has further been discovered by the inventors of the present invention that co-action activity exists between CPC and the $E_H$-raising compound and the zinc compound. For example, co-action activity exists between CPC, sodium chlorite and a zinc compound. The oral composition with CPC has an enhanced beneficial (i.e. more than additive) effect for the subject compared to the oral composition without CPC. For example, statistical analysis demonstrates that the oral composition containing CPC has an enhanced effect to reduce oral malodor, and has an enhanced anti-gingivitis, anti-plaque and anti-tartar (calculus) effect compared to the oral composition without CPC. See FIGS. 3 and 4.

The present disclosure also provides an article of manufacture comprising a packaging material and one or more of the oral compositions described herein contained within the packaging material. The packaging material used to contain the oral compositions can comprise glass, plastic, metal or any other suitably inert material. For example, a dentifrice containing the oral composition may be contained in a collapsible tube, such as aluminum, or plastic, or a squeeze, pump, or pressurized dispenser for measuring out the contents or in a tearable sachet. Furthermore, the packaging material can be capable of retaining the zinc compound and the $E_h$-raising compound separately, such that they can be mixed prior to use of the oral composition. Moreover, any of the above-described optional components or combinations thereof may be premixed with any of the first and second components, or the cetylpyridinium chloride. Alternatively, any of the above-described optional components or combinations thereof may be stored separately from the first and second components. As such, the optional compound, the zinc compound, $E_h$-raising compound, and the cetylpyridinium chloride are all mixed prior to use of the oral composition.

Separate compositions can optionally be co-packaged, for example in a single container or in a plurality of containers. For example, separate containers for the zinc compound and $E_h$-raising compound utilized. The separate containers can also be presented to a consumer separately and independently, for use according to methods described herein.

EXAMPLE

Oral compositions in accordance with the present disclosure are formulated for various evaluations. For all Formulations (1-12), the pH range of Solution 1 is from about 7.0 to about 7.65; and the pH range of Solution 2 is from about 4.2 to about 4.8.

Example 1

| | | Formulation I | |
|---|---|---|---|
| Solution 1 | water | 982620 (mg/L) | 98.262% |
| | benzoate buffer | 16005 | 1.60% |
| | sodium chlorite | 1375 | 0.1375% |

-continued

| Formulation I | | | |
|---|---|---|---|
| Solution 2 | water | 831640 | 83.164% |
| | glycerin | 120000 | 12.000% |
| | inactive ingredients | 39560 | 3.956% |
| | benzoate buffer | 2600 | 0.260% |
| | zinc chloride | 5200 | 0.520% |
| | CPC | 1000 | 0.100% |

Example 2

| Formulation II | | | |
|---|---|---|---|
| Solution 1 | water | 982620 (mg/L) | 98.262% |
| | benzoate buffer | 12030 | 1.20% |
| | sodium chlorite | 5350 | 0.5350% |
| Solution 2 | water | 843640 | 84.364% |
| | glycerin | 112000 | 11.200% |
| | inactive ingredients | 39560 | 3.956% |
| | benzoate buffer | 2500 | 0.250% |
| | zinc chloride | 1300 | 0.130% |
| | CPC | 1000 | 0.100% |

Example 3

| Formulation III | | | |
|---|---|---|---|
| Solution 1 | water | 982620 (mg/L) | 98.262% |
| | benzoate buffer | 16695 | 1.67% |
| | sodium chlorite | 685 | 0.0685% |
| Solution 2 | water | 836840 | 83.684% |
| | glycerin | 114000 | 11.400% |
| | inactive ingredients | 39560 | 3.956% |
| | benzoate buffer | 2700 | 0.270% |
| | zinc chloride | 5900 | 0.590% |
| | CPC | 1000 | 0.100% |

Example 4

| Formulation IV | | | |
|---|---|---|---|
| Solution 1 | water | 982620 (mg/L) | 98.262% |
| | benzoate buffer | 14420 | 1.44% |
| | sodium chlorite | 2960 | 0.2960% |
| Solution 2 | water | 824940 | 82.494% |
| | glycerin | 128000 | 12.800% |
| | inactive ingredients | 39560 | 3.956% |
| | benzoate buffer | 2800 | 0.280% |
| | zinc chloride | 3700 | 0.370% |
| | CPC | 1000 | 0.100% |

Example 5

| Formulation V | | | |
|---|---|---|---|
| Solution 1 | water | 982620 (mg/L) | 98.262% |
| | benzoate buffer | 14080 | 1.41% |
| | sodium chlorite | 3300 | 0.3300% |
| Solution 2 | water | 827540 | 82.754% |
| | glycerin | 126000 | 12.600% |

-continued

| Formulation V | | | |
|---|---|---|---|
| | inactive ingredients | 39560 | 3.956% |
| | benzoate buffer | 2900 | 0.290% |
| | zinc chloride | 3000 | 0.300% |
| | CPC | 1000 | 0.100% |

Example 6

| Formulation VI | | | |
|---|---|---|---|
| Solution 1 | water | 982620 (mg/L) | 98.262% |
| | benzoate buffer | 12655 | 1.27% |
| | sodium chlorite | 4725 | 0.4725% |
| Solution 2 | water | 839040 | 83.904% |
| | glycerin | 115000 | 11.500% |
| | inactive ingredients | 39560 | 3.956% |
| | benzoate buffer | 3000 | 0.300% |
| | zinc chloride | 2400 | 0.240% |
| | CPC | 1000 | 0.100% |

Example 7

| Formulation VII | | | |
|---|---|---|---|
| Solution 1 | water | 982620 (mg/L) | 98.262% |
| | benzoate buffer | 13530 | 1.353% |
| | sodium chlorite | 3850 | 0.3850% |
| Solution 2 | water | 843640 | 84.364% |
| | glycerin | 110000 | 11.00% |
| | inactive ingredients | 39560 | 3.956% |
| | benzoate buffer | 2500 | 0.25% |
| | zinc chloride | 3300 | 0.33% |
| | CPC | 1000 | 0.10% |

Example 8

| Formulation VIII | | | |
|---|---|---|---|
| Solution 1 | water | 982620 (mg/L) | 98.2620% |
| | benzoate buffer | 13130 | 1.313% |
| | sodium chlorite | 4250 | 0.425% |
| Solution 2 | water | 825100 | 82.51% |
| | glycerin | 126500 | 12.65% |
| | inactive ingredients | 39600 | 3.96% |
| | benzoate buffer | 5000 | 0.50% |
| | zinc chloride | 2800 | 0.28% |
| | CPC | 1000 | 0.10% |

Example 9

| Formulation IV | | | |
|---|---|---|---|
| Solution 1 | water | 982620 (mg/L) | 98.2620% |
| | benzoate buffer | 14805 | 1.481% |
| | sodium chlorite | 2575 | 0.258% |
| Solution 2 | water | 843640 | 84.36% |
| | glycerin | 106500 | 10.65% |
| | inactive ingredients | 39600 | 3.96% |
| | benzoate buffer | 7360 | 0.74% |

-continued

Formulation IV

| | | | |
|---|---|---|---|
| zinc chloride | | 1900 | 0.19% |
| CPC | | 1000 | 0.10% |

Example 10

Formulation X

| | | | | |
|---|---|---|---|---|
| Solution 1 | water | 982620 | (mg/L) | 98.2620% |
| | benzoate buffer | 15430 | | 1.543% |
| | sodium chlorite | 1950 | | 0.195% |
| Solution 2 | water | 832400 | | 84.364% |
| | glycerin | 119000 | | 11.90% |
| | inactive ingredients | 39600 | | 3.96% |
| | benzoate buffer | 4000 | | 0.40% |
| | zinc chloride | 4000 | | 0.40% |
| | CPC | 1000 | | 0.10% |

Example 11

Formulation XI

| | | | | |
|---|---|---|---|---|
| Solution 1 | water | 982620 | (mg/L) | 98.2620% |
| | benzoate buffer | 16290 | | 1.6290% |
| | sodium chlorite | 1090 | | 0.1090% |
| Solution 2 | water | 843640 | | 84.364% |
| | glycerin | 109000 | | 10.90% |
| | inactive ingredients | 39600 | | 3.96% |
| | benzoate buffer | 4760 | | 0.48% |
| | zinc chloride | 2000 | | 0.20% |
| | CPC | 1000 | | 0.10% |

Example 12

Formulation XII

| | | | | |
|---|---|---|---|---|
| Solution 1 | water | 982620 | (mg/L) | 98.2620% |
| | benzoate buffer | 11430 | | 1.143% |
| | sodium chlorite | 5950 | | 0.595% |
| Solution 2 | water | 843640 | | 84.364% |
| | glycerin | 102500 | | 10.25% |
| | inactive ingredients | 39600 | | 3.96% |
| | benzoate buffer | 12460 | | 1.25% |
| | zinc chloride | 800 | | 0.08% |
| | CPC | 1000 | | 0.10% |

Example 13—Cysteine Challenge Testing

Cysteine challenge testing is in vivo methodology designed to: (1) stimulate a significant production of VSCs in the mouth, simulating a severe halitosis condition; and (2) evaluate the degree to which a test product/ingredient can prevent the formation of these VSCs, thereby preventing bad breath. In such testing, a subject rinses with a specified amount of a solution containing cysteine. Cysteine is an amino acid that acts as a food source for, and is immediately metabolized by, Gram-negative anaerobic bacteria. The by-product of this bacterial metabolism is hydrogen sulfide, the fastest-forming and most prevalent component of VSCs. Under normal circumstances in the presence of cysteine, Gram-negative anaerobes will generate dramatically high levels of VSCs. Such increases in VSCs ("spikes") are evaluated before and after administering a test rinse ("test rinse") to determine that test rinse's short and long-term affect on VSC production.

The first step in the cysteine challenge test is to measure the subject's initial, pre-test VSC level in ppb with a Halimeter. Before rinsing with any test rinse, a subject rinses with a cysteine solution for 25 seconds, gargles for 5 seconds (for a total of 30 seconds), and the VSC level is measured again in ppb ("pre-test spike"). After any cysteine rinse, the VSC level gradually returns to a minimum value ("baseline value") as the cysteine is depleted. Generally this takes approximately twenty minutes. Any post-cysteine rinse measurement that falls at or below 350 ppb is considered a baseline value (based upon the statistical analysis of the present study). Once at baseline value after the very first cysteine rinse, the test subject is administered the test rinse and VSC measurements are taken again. The subject rinses with a cysteine solution numerous times over the remaining test period to determine whether or not a spike occurs ("post-test spike") at each testing point, typically at 20 to 180 minute intervals for a total period of 540 minutes.

The presence or absence of post-test spikes indicates whether or not a test rinse inhibits the ability of Gram-negative anaerobes to metabolize cysteine and produce VSCs, and if so, if such inhibition continues over time. If the first cysteine rinse administered after the test rinse results in a post-test spike ("first post-test spike") that is approximately at the same level of the concurrent pre-test spike, it establishes that the test rinse does not inhibit the anaerobes' metabolism of cysteine or production of VSCs. Conversely, when the first cysteine challenge administered after the test rinse results in no post-rest spike, it establishes that the test rinse does inhibit the ability of the anaerobes to metabolize cysteine and produce VSCs. The ongoing presence or absence of post-test spikes with additional cysteine challenges determines whether or not a test rinse has a long-term affect on such anaerobes and their VSC production.

The results of cysteine challenge testing (clinically generated bad breath) are also correlated with the results of organoleptic testing (naturally occurring bad breath) with respect to the prevention of bad breath by test rinses.

Specifically, cysteine challenge testing was used to measure the effectiveness of four mouthwashes: a placebo (distilled water), a commercially available mouthwash (Listerine®), another commercially available mouthwash (SmartMouth®), and SmartMouth ACF™. The correlation between cysteine challenge testing of all test rinses and organoleptic testing in corresponding, previously published, double-blind clinical studies ("previous studies") was then evaluated.

Distilled water, as the control in this study, does not contain any ingredient that would affect Gram-negative anaerobes or their ability to metabolize amino acids. This would explain why double-blind clinical studies utilizing organoleptic testing have demonstrated that a distilled water control does not provide fresh breath/prevent bad breath longer than one hour.

Five adult subjects participate in a screening visit. During the screening visit, the candidate signs an Informed Consent Form, is asked pertinent medical questions, signs a non disclosure agreement (NDA), and fills out a demographic form.

A candidate is accepted into the study after passing the inclusion/exclusion criteria checklist, which follows a dental screening that is administered by a licensed, practicing dentist. The subject is given written instructions listing certain dietary and oral hygiene restrictions to be followed in preparation for the test. Two weeks prior to testing and during the test period, the subject must refrain from using any oral hygiene products outside of brushing with the standard toothpaste (Colgate®) and flossing. On the morning of test visits, the subject does not brush or use any oral hygiene products and does not consume a beverage.

The Halimeter is recalibrated prior to each test run, set to 0.0 ppb and checked for stability. The Halimeter is adjusted to read 0.0 ppb as necessary. A sample of oral headspace (air) is taken by placing the tip of a straw attached to the Halimeter into the posterior one third of the mouth, one centimeter above the tongue, with the lips slightly parted. The straw is not touched by the subject's lips, teeth, or tongue. The subject is instructed to breathe as necessary through the nose and not to blow into the straw. The maximum, peak reading is recorded.

At each test visit, a subject's initial, pre-test VSC level (in ppb) is established by taking three consecutive readings with the Halimeter.

The subject rinses with 5 mL of a 6 mM Cysteine solution for 25 seconds, gargles for 5 seconds (for a total of 30 seconds), and expectorates. The next reading is taken immediately. Four more readings are taken at five minute intervals (20 minutes total).

The subject rinses vigorously with either 10 mL of one single unit of the test material or 5 ml each of a two-unit test material (mouthwash or control), for 30 seconds, gargles for 15 seconds (for a total of 45 seconds) and expectorates. Neither the subject nor tester knows what test rinse is being administered. After 10 minutes, the next reading is taken. Four more readings are taken at five minute intervals (20 minutes total).

The subject rinses with 5 mL of a 6 mM Cysteine solution for 25 seconds, gargles for 5 seconds (for a total of 30 seconds), and expectorates. The next reading is taken immediately. Four more readings are taken at five minute intervals (20 minutes total).

The subject rinses with 5 mL of a 6 mM Cysteine solution for 25 seconds, gargles for 5 seconds (for a total of 30 seconds), and expectorates. The next reading is taken immediately. Eight more readings are taken at ten minute intervals (80 minutes total).

The subject rinses with 5 mL of a 6 mM Cysteine solution for 25 seconds, gargles for 5 seconds (for a total of 30 seconds), and expectorates. The next reading is taken immediately. Nine more readings are taken at twenty minute intervals (180 minutes total).

The subject rinses with 5 mL of a 6 mM Cysteine solution for 25 seconds, gargles for 5 seconds (for a total of 30 seconds), and expectorates. The next reading is taken immediately. Six more readings are taken at ten minute intervals (60 minutes total).

The subject rinses with 5 mL of a 6 mM Cysteine solution for 25 seconds, gargles for 5 seconds (for a total of 30 seconds), and expectorates. The next reading is taken immediately. Six more readings are taken at ten minute intervals (60 minutes total).

The subject rinses with 5 mL of a 6 mM Cysteine solution for 25 seconds, gargles for 5 seconds (for a total of 30 seconds), and expectorates. The next reading is taken immediately. Six more readings are finally taken at ten minute intervals (60 minutes total).

The testing time, not including mixing, rinsing, and so forth totals 500 minutes.

Figure 2:
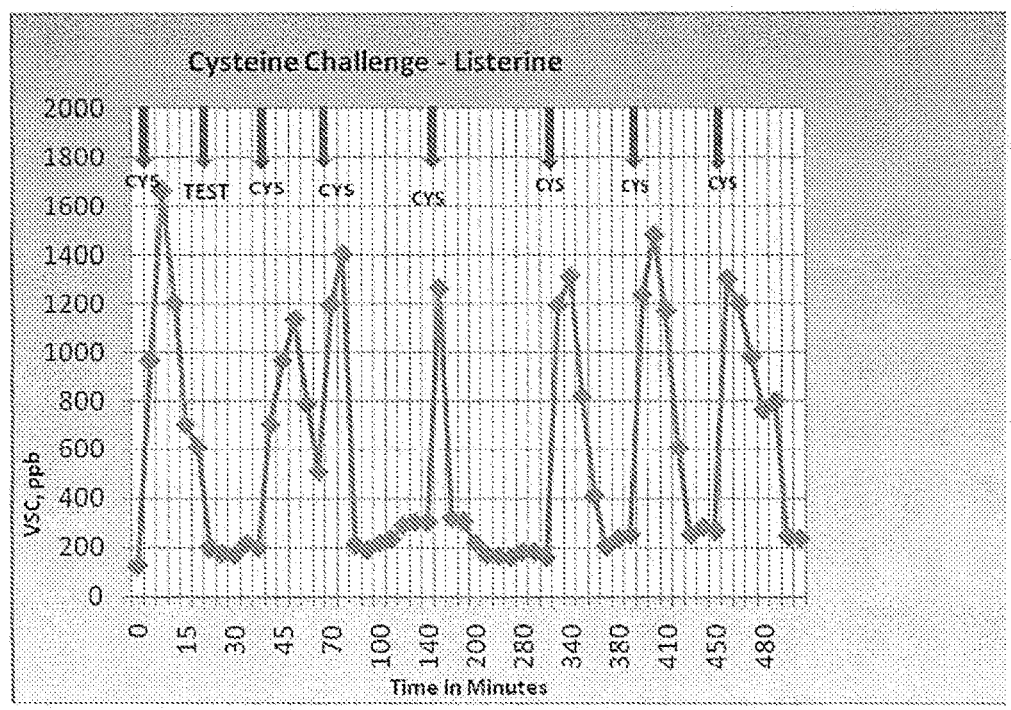
FIG. 2 is the same as FIG. 1, except the subjects were tested with Listerine®.

Two examples of Halimeter output are shown in FIGS. 1 and 2 from subjects being tested with distilled water and Listerine® respectively. The Figures correspond to graphs of Halimeter output of VSC in units of ppb shown on the vertical axis and time in minutes shown on the horizontal axis.

For the cysteine challenge using distilled water as the mouthwash (shown in FIG. 1), the average of the 14 "high VSC values" above 1000 ppb on the vertical axis correspond to 1360±199 (15%). Similarly, when using Listerine® as the mouthwash (shown in FIG. 2), the 13 "high VSC values above 1000 ppb on the vertical axis correspond to 1290±149 (12%). The statistical results of the cysteine challenge testing procedure with Listerine® and distilled water (Tables 1 and 2 below) are indistinguishable. Thus, Listerine® is no better at preventing the formation of VSC in the mouth than distilled water.

TABLE 1

Comparison of Cysteine Challenge Testing to Distinguish Potential Differences between Distilled Water and Listerine ® in the Removal of VSCs from the Breath

| Sample | Graph 1 Maximum >1000 VSC | Graph 2 Maximum >1400 VSC | All Samples Tested 5 subjects | Conclusions |
|---|---|---|---|---|
| $H_2O$ | 1360 ± 199 | 1505 ± 61 | 1568 ± 88 | No Difference |
| Listerine ® | 1290 ± 149 | 1517 ± 132 | 1571 ± 142 | No Difference |

TABLE 2

Comparison of Cysteine Challenge Testing to Show Similarity in Distilled Water and Listerine ® Samples in the Removal of VSCs from the Breath

| Sample | Graph 1 Minimun <400 VSC | Graph 2 Minimun <400 VSC | All Samples Tested 5 Subjects | Conclusions |
|---|---|---|---|---|
| $H_2O$ | 205 ± 23 | 205 ± 23 | 173 ± 38 | No Difference |
| Listerine ® | 196 ± 40 | 196 ± 40 | 181 ± 32 | No Difference |

Specifically, the results shown in FIG. 3 confirm the results of previous cysteine challenge studies that demonstrated the use of SmartMouth® results in markedly extended periods of time of VSC values below 400 ppb (>120 minutes) and more than 500 minutes of VSC values below 600 ppb.

The distribution of the time-dependant data (Halimeter Base-Line and Peak Values) are Gaussian and the resulting "array" can best be summarized by reporting the Average (also known as the Mean) and the Standard Deviation from the Average. These results are reported as the Average/Median±the Standard Deviation.

All of the measurements reported can readily be placed into two distinct groups: (a) a mouth rinse that will reduce the number of Gram-negative anaerobes to a sufficient degree, or for a long enough period of time, to provide fresh breath less than one hour/prevent bad breath no longer than one hour and (b) a mouth rinse that provides fresh breath longer than 6-12 hours (and in some examples even longer).

The Halimeter data collected in this study were "well-behaved." For the purposes of comparing similarities and differences in mouthwashes of varying characteristics, the statistical concept of "two different groups" suffices.

The reporting limits are in the 10-15% level (for one standard deviation from the Mean) which is sufficiently accurate to distinguish differences between various mouthwashes differing in their "Fresh Breath" characteristics of less than one hour, or greater than 12 hours.

As noted above, the baseline values for SmartMouth® over the period of 25-500 minutes correspond to 195±96 ppb (49%) and are typical and consistent with our expectations. However, FIG. 4 for ACF shows that all baseline values are at levels not exceeding 275 ppb during the entire 30-500 minute cysteine challenge testing period, including immediately after each of the six individual cysteine rinses. This result has never been observed or reported previously. This is clear evidence of a enhanced effect, such as co-action activity, between SmartMouth® and SmartMouth ACF™.

Additional comparisons with respect to this co-action are tabulated in Table 3. By using the statistical information collected during the cysteine challenge testing, it is possible to calculate the "long-term fresh breath potential" of a test rinse. Based on the Halimeter measurements reported in this study, direct comparisons show the time it will take (in minutes) to reach 25%, 50% or 70% of the post-test spike with water, Listerine®, SmartMouth®, or SmartMouth ACF™. Longer times denote longer fresh breath.

TABLE 3

Summary of Average Cysteine Challenge Testing Results
(Average Time Required to Return to 25%, 50%, and 75% of Pre-Test Spike)

| % of Pre-Test Rinse Spike (Correlating Halimeter ppb) | At Least 25% (500 ppb) | At Least 50% (850 ppb) | At Least 75% (1200 ppb) |
|---|---|---|---|
| Water | 45-50 Minutes | 45-50 Minutes | 45-50 Minutes |
| Listerine ® | 45-50 Minutes | 45-50 Minutes | 45-50 Minutes |
| SmartMouth ® | 345-380 Minutes | 345-380 Minutes | 345-380 Minutes |
| SmartMouth ACF ™ | >500 Minutes | >500 Minutes | >500 Minutes |

With a water rinse given as a control, there was minimal change in the high VCS readings resulting from subsequent cysteine challenges (1500±75 ppb). When Listerine® was used as the mouthwash, again, there was minimal change in the high VCS readings. When the test was given with SmartMouth®, there was a significant reduction in VSC levels with each subsequent cysteine challenge all the way to the 500 minute limit.

Furthermore, when the cysteine challenge test was given with SmartMouth ACF™, there was a continuous and an even more significant lowering of the VSC levels continuing with each subsequent cysteine challenge to the 500 minute limit of these studies.

This study demonstrates that distilled water and Listerine® do not impair the ability of Gram-negative anaerobes to metabolize cysteine and produce VSCs. With both of these test rinses, the first post-test spike (and all subsequent spikes) increases to approximately the same levels of the pre-test spike. This demonstrates that the ability of Gram-negative anaerobes to metabolize amino acids and produce VSCs has been unaffected by these rinses. These results are consistent and can be correlated with previous studies which prove that neither distilled water nor Listerine® provide fresh breath/prevent bad breath for longer than one hour.

This study also demonstrates that SmartMouth® significantly impairs the ability of Gram-negative anaerobes to metabolize cysteine and produce VSCs over an extended period of time. With SmartMouth®, the first two post-test cysteine challenges did not result in any spike and no subsequent spike reached even 50% of pre-test spike levels. This demonstrates that the ability of Gram-negative anaerobes to metabolize amino acids and produce VSCs has been dramatically inhibited by SmartMouth®. This result is consistent and can be correlated with a previous study which proved that SmartMouth® provides fresh breath/prevents bad breath for at least 12 hours.

Figure 3:
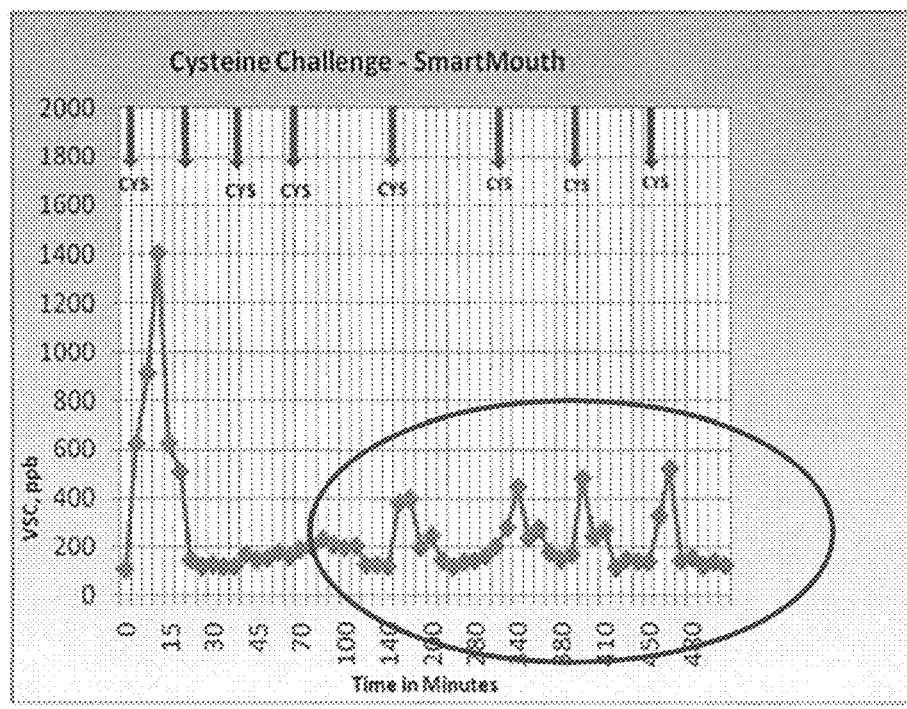
FIG. 3 is the same as FIG. 1, except the subjects were tested with SmartMouth®.
Figure 4:
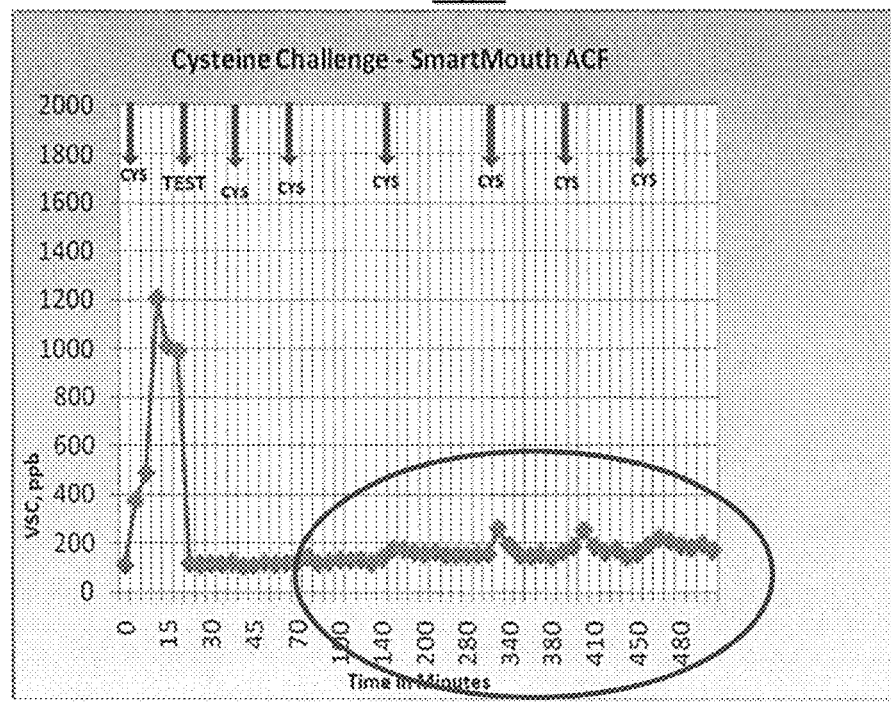
FIG. 4 is the same as FIG. 1, except the subjects were tested with SmartMouth Advanced Clinical Formula (ACF) (SmartMouthACF™).

A comparison of the cysteine challenge testing properties of SmartMouth® and SmartMouth ACF™ was evaluated to determine if a correlation existed between the previous SmartMouth® study and the cysteine challenge testing of SmartMouth ACF™ FIG. 3 (SmartMouth®) shows that (1) the first post-test rinse spike occurred at approximately 160 minutes and reached approximately 30% of the pre-test spike, and (2) the last post-test rinse spike occurred at approximately 470 minutes and reached approximately 41% of the pre-test spike. In comparison, FIG. 4 (SmartMouth ACF™) shows that (1) the first post-test rinse spike occurred at approximately 320 minutes and reached approximately 25% of the pre-test spike, and (2) the last post-test rinse spike occurred at approximately 470 minutes and never exceeded 25% of the pre-test spike. This demonstrates, both initially and over time, that SmartMouth ACF™ has a greater effect on the ability of Gram-negative anaerobes to metabolize amino acids and produce VSCs, than SmartMouth®. This study has demonstrated that the CPC in SmartMouth ACF™ also does not inhibit the zinc ion technology. In fact, CPC enhances the zinc ion effect in SmartMouth ACF™. An enhanced effect is observed when CPC is used, such that a co-action exists between ingredients.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A method for reducing oral malodor in a non-human animal, comprising delivering an oral composition to an oral cavity of the non-human animal, wherein the oral composition comprises:
    a first component comprising at least one $E_h$-raising compound and a pharmaceutically acceptable carrier; and
    a second component comprising at least one zinc compound, cetylpyridinium chloride (CPC) and a pharmaceutically acceptable carrier.

2. The method of claim 1, further comprising mixing the first component and the second component prior to delivering the oral composition to the oral cavity in the non-human animal.

3. The method of claim 1, wherein the at least one $E_h$-raising compound is selected from the group consisting of hydrogen peroxide, a fermentable sugar, an oxyhalogen compound, a biologically-compatible oxidation-reduction buffer, and combinations thereof.

4. The method of claim 1, wherein the at least one zinc compound is selected from the group consisting of zinc chloride, zinc acetate, zinc salicylate, zinc sulfate, zinc nitrate, and combinations thereof.

5. The method of claim 1, wherein the at least one $E_h$-raising compound is selected from the group consisting of hydrogen peroxide, sodium chlorite and a fermentable sugar; and the zinc compound is selected from the group consisting of zinc chloride and zinc acetate.

6. The method of claim 1, wherein a pH of the first component ranges from about 7.0 to about 8.5, and a pH of the second component ranges from about 3.0 to about 6.0.

7. The method of claim 1, wherein the first component comprises about 0.01% by weight to about 3.0% by weight of the at least one $E_h$-raising compound, and wherein the second component comprises about 0.02% by weight to about 1.0% by weight of zinc ion and about 0.02% by weight to about 0.6% by weight of CPC.

8. The method of claim 1, wherein the first component comprises about 0.04% by weight to about 1.2% by weight of sodium chlorite and a pH of the first component ranges from about 7.0 to about 8.5, and wherein the second component comprises about 0.04% by weight to about 0.7% by weight of zinc ion and about 0.09% by weight to about 0.2% by weight of CPC and a pH of the second component ranges from about 3.0 to about 6.0.

9. The method of claim 1, wherein the non-human animal is a domestic animal, livestock or exotic wildlife.

10. The method of claim 9, wherein the domestic animal is a dog or cat.

11. The method of claim 1, wherein the oral composition is in the form of a solid, liquid, spray, gel, foam, syrup or powder.

12. The method of claim 11, wherein the oral composition is orally delivered through a dental care product, a food product, a tablet, a capsule, a flash-melt formulation, a confection, a lozenge, a toothpaste, a mouthrinse, a breath spray, a mint and/or a chew toy.

13. The method of claim 1, wherein the oral composition is orally delivered from one to five times per day.

* * * * *